United States Patent [19]

Harata et al.

[11] Patent Number: 4,509,035

[45] Date of Patent: Apr. 2, 1985

[54] HUMIDITY-SENSITIVE ELEMENT AND PROCESS FOR PRODUCING THE SAME

[75] Inventors: Mituo Harata; Hideaki Hiraki, both of Kawasaki; Shigeki Uno; Kazuo Sakuma, both of Tokyo; Kiyosi Matsunaga, Yokohama, all of Japan

[73] Assignee: Tokyo Shibaura Denki Kabushiki Kaisha, Kawasaki, Japan

[21] Appl. No.: 556,598

[22] Filed: Nov. 30, 1983

[30] Foreign Application Priority Data

Nov. 30, 1982 [JP] Japan .................. 57-209605

[51] Int. Cl.$^3$ ............................................. H01L 7/00
[52] U.S. Cl. ...................................... 338/35; 73/336.5
[58] Field of Search ................. 338/34, 35; 73/335, 73/336.5; 340/602

[56] References Cited

U.S. PATENT DOCUMENTS

| 4,052,691 | 10/1977 | Nagano et al. | 338/35 |
| 4,343,688 | 8/1982 | Harwood | 338/35 X |
| 4,424,508 | 1/1984 | Harata et al. | 338/35 |

FOREIGN PATENT DOCUMENTS 57-34301  2/1982  Japan .

Primary Examiner—Roy N. Envall, Jr.
Assistant Examiner—C. N. Sears
Attorney, Agent, or Firm—Oblon, Fisher, Spivak, McClelland & Maier

[57] ABSTRACT

A humidity-sensitive element which has excellent humidity-sensitive characteristics and has a small drift after being exposed to a high humidity for a long period of time. The humidity-sensitive element of the invention includes a porous metal oxide sintered body, a simple substance or an oxide of phosphorus or sulfur carried on the porous metal oxide sintered body, and copper ions carried on the porous metal oxide sintered body.

7 Claims, 11 Drawing Figures

F I G. 3
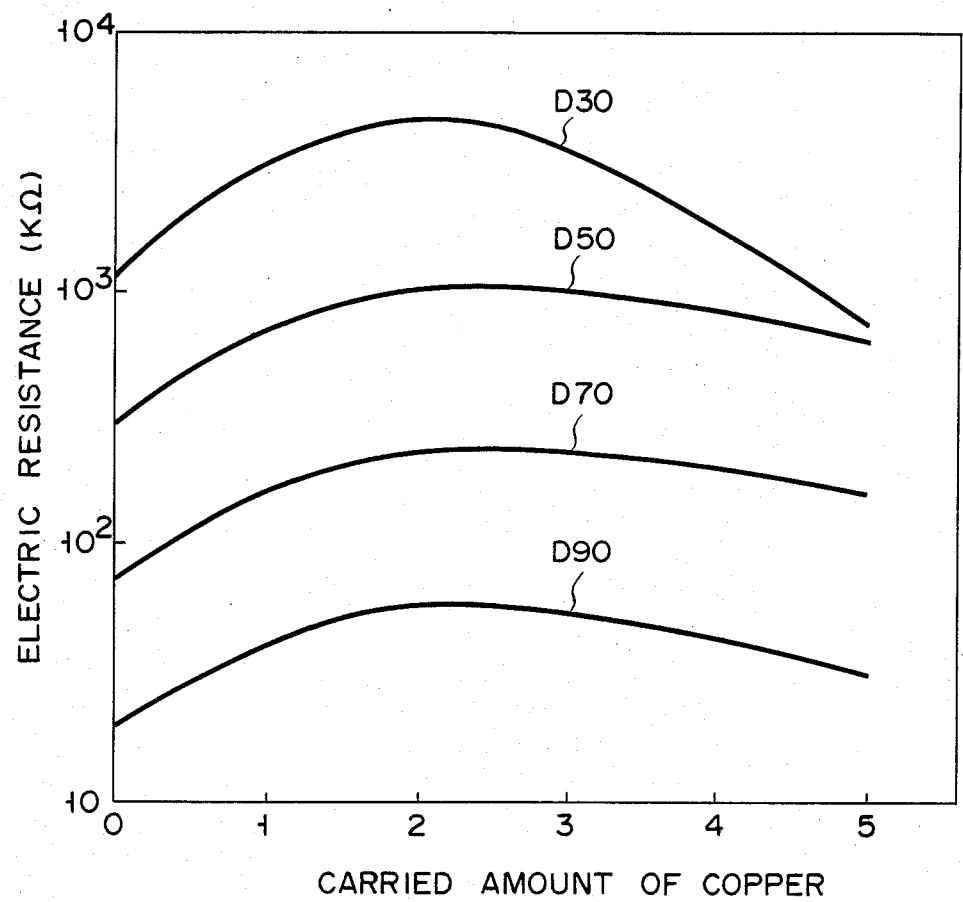

ns a humidity-sensitive element.

HUMIDITY-SENSITIVE ELEMENT AND PROCESS FOR PRODUCING THE SAME

BACKGROUND OF THE INVENTION

I. Field of the Invention

The present invention relates to a humidity-sensitive element.

II. Description of the Prior Art

Various types of devices are known for measuring the water vapor content in the air, that is, humidity. A psychrometer is a typical example of such devices and is inexpensive. However, the psychrometer requires periodic maintenance such as a supply of water. A device for measuring humidity is known which uses a microwave or a laser beam and which measures the humidity in accordance with the absorption and scattering of such electromagnetic waves by water vapor. However, such devices are large in size and are expensive, and for these reasons are not generally used.

Humidity-sensitive elements which utilize the adsorption of water vapor on the surface of (or inside) a solid material have been recently proposed, and some elements of this type are commercially available. Such an element provides a measurement in accordance with a change in an electric resistance due to a change in the humidity. This type of element has a simple structure and is easy to handle, and provides a measurement of (a change in) humidity in the form of an electric signal. For this reason, application of such an element in various different fields is expected.

The use of humidity-sensitive polymers and porous metallic oxides as a material for such a humidity-sensitive element has been widely discussed.

When a porous metal oxide is used, the powder of a selected metal oxide is sintered at a high temperature. A gold paste or ruthenium oxide paste as an electrode material is baked on the element at 800° C. and is securely adhered thereto. The element has no tendency of electrode separation or the like, and the element provides stable operation.

The electric resistance of a metal oxide sintered body which changes in response to a change in humidity is the surface resistance as described above. A change in the electric resistance of such a material is considered to be attributable to the migration of protons present on the surface of or on internal pore inner surfaces of the sintered body through a medium of water molecules introduced by adsorption. In other words, the surface resistance is influenced by the number and mobility of protons, which factors change in accordance with the number of adsorbed water molecules (as a function of humidity). In most cases, a metal oxide, whether a p- or n-type semiconductor or insulator, has, at normal temperature, a smaller surface resistance or electric resistance with an increase in humidity (with an increase in the number of adsorbed water molecules).

However, the water molecules, which are initially in a physically adsorbed state, are shifted to a chemically adsorbed state as time elapses. Then, the mobility of protons in the humidity-sensitive element is decreased, thereby increasing the surface resistance or electric resistance of the element. In addition, when the surface of or pore inner surfaces of the humidity-sensitive element adsorbs together with water vapor a small amount of oil mist, dust, or gases, the humidity-sensitive resistance range of the element may change or, in some cases, the element may subsequently fail to exhibit humidity-sensitive characteristics (response in an electric resistance to a change in humidity).

In order to solve such problems, a method (heating cleaning method) has been proposed. According to this method, a heater is arranged to surround a humidity-sensitive element. Prior to actual operation of the humidity-sensitive element, the element is sufficiently heated so as to eliminate therefrom chemically adsorbed water molecules, oil mist, dust, or gases, thereby providing a humidity-sensitive element having initial characteristics. Although this cleaning method can provide a high detection precision, it does not allow measurement while the element is being cleaned. In other words, this method prevents continuous measurement. However, a method is plausible wherein the surface of a metal oxide is modified by a suitable surface treatment. Continuous measurement is enabled by thus utilizing reversible physical adsorption/desorption of water.

A method described in Japanese Patent Disclosure (Kokai) No. 57-34301 and the like proposes the carrying of a simple substance of phosphorus or sulfur or an oxide thereof on the surface of a metal oxide so as to stabilize humidity-sensitive characteristics of the element. This method allows continuous measurement over a long period of time when the element is placed in the air. However, when the element is exposed to a high humidity of 90% for a long period of time, the output drift is significant.

SUMMARY OF THE INVENTION

It is, therefore, an object of the present invention to provide a humidity-sensitive element which has excellent humidity-sensitive characteristics and which has high performance with a small range of drift over a long period of time, and also to provide a process for producing the same.

In order to achieve the above object, there is provided a humidity-sensitive element comprising a porous metal oxide sintered body, a simple substance or an oxide of an element selected from the group consisting of phosphorus and sulfur, the simple substance or the oxide being carried on said porous metal oxide sintered body, and copper ions carried on said porous metal oxide sintered body.

There is also provided according to the present invention, a process for producing a humidity-sensitive element, including the steps of: preparing a metal oxide powder for a porous metal oxide sintered body; milling the metal oxide powder with a binder to provide a milled substance; sintering the milled substance to provide a sintered element; forming electrodes on the sintered element; impregnating the sintered element with electrodes formed thereon with a solution containing phosphorus and/or sulfur and copper ions; and heating the sintered element impregnated with the solution.

The humidity-sensitive element of the present invention has a small drift and a high reliability upon being left for a long period of time, since it has excellent humidity-sensitive characteristics. The elements of the present invention have only small variations in humidity-sensitive characteristics and therefore provide a high yield.

BRIEF DESCRIPTION OF THE DRAWINGS

FIG. 3 is a graph showing the electrical resistance as a function of the carried amount of copper of the humidity-sensitive element of Example 3 under humidities of 30%, 50%, 70% and 90%;

DETAILED DESCRIPTION OF THE PREFERRED EMBODIMENTS

Figure 2:
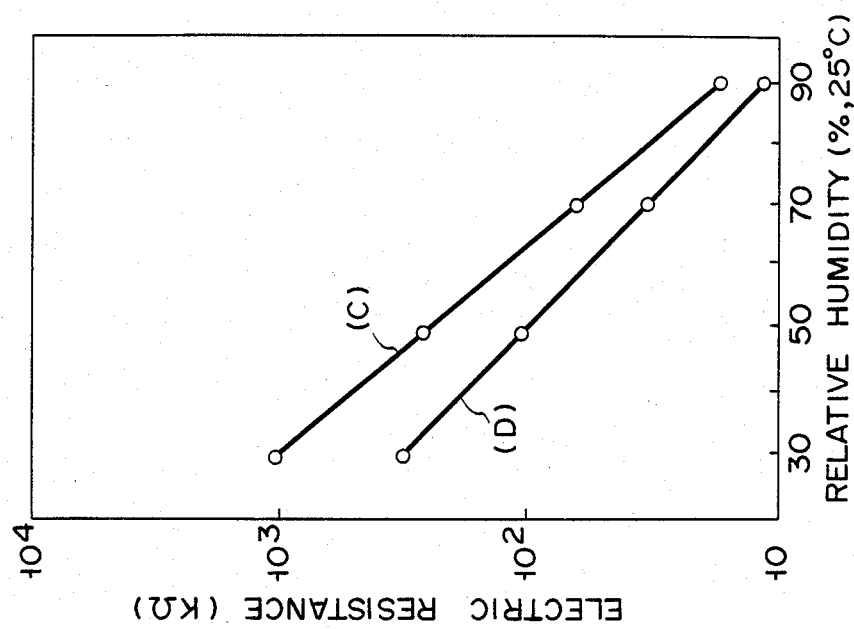
FIG. 2 is a graph showing the initial humidity-sensitive characteristics of a humidity-sensitive element of Comparative Example 1, and the same characteristics after the element is left to stand under the same conditions as in Example 1 for 200 hours.

A porous metal oxide sintered body of the present invention consists of any material which has humidity sensitivity. Ordinarily, such a materials is selected from zinc oxide (ZnO), ferric oxide ($Fe_2O_3$), stannic oxide ($SnO_2$), magnesia (MgO), chromium oxide ($Cr_2O_3$), barium oxide (BaO), titanium dioxide ($TiO_2$), or tri-iron tetroxide ($Fe_3O_4$); or a compound oxide thereof.

When a porous metallic oxide sintered body consists of a mixture of 5 to 50 mol % of zinc oxide, 30 to 90 mol % of titanium dioxide and 5 to 20 mol % of chromium oxide, a humidity-sensitive element having a wide range of resistance change can be obtained. When the amounts of the zinc oxide, titanium dioxide and chromium oxide fall outside the above ranges, a humidity-sensitive element having a wide range of resistance change may not be obtained. In particular, when the amount of zinc oxide exceeds 50 mol %, the electric resistance of the humidity-sensitive element is increased. When the amount of chromium oxide exceeds 20 mol %, sintering performance is degraded and handling of the element is difficult. On the other hand, when the amount of chromium oxide is less than 5 mol %, a satisfactory porous layer may not be obtained.

When a porous metal oxide sintered body consists of 99 to 70 mol % of titanium dioxide and 1 to 30 mol % of alumina, or 99 to 70 mol % of titanium dioxide and 1 to 30 mol % of magnesia, a humidity-sensitive element having a sufficiently wide range of resistance change can also be obtained. In this case also, if the amounts of titanium dioxide, alumina and magnesia fall outside the above ranges, a humidity-sensitive element having good characteristics may not be obtained. In particular, when the amount of titanium dioxide exceeds 99 mol %, the electric resistance of the element generally becomes too high. When the amount of alumina or magnesia exceeds 30 mol %, sintering performance may be degraded.

When a porous metal oxide sintered body consists of 99 to 70 mol % of titanium dioxide and 1 to 30 mol % of chromium oxide, tungsten oxide, molybdenum oxide, tantalum oxide, niobium oxide, vanadium oxide or a mixture thereof, a humidity-sensitive element having a wide resistance change range in a low resistance range can be obtained. When the range of resistance change of a humidity-sensitive element is within a high resistance range (e.g., about 3 $M\Omega$), a special circuit is required to convert such a resistance into a low resistance, resulting in an expensive element. However, if a porous metal oxide sintered body having the composition as described immediately above is used, such a special circuit need not be incorporated and an inexpensive element can be obtained. In this case, however, if the amount of titanium dioxide exceeds 99 mol %, a low resistance change range may not be obtained and a large drift may be obtained. On the other hand, if the amount of titanium dioxide is less than 70 mol %, again a low resistance change range may not be obtained. In this case, the stability under high levels of humidity may be impaired, sintering performance may be poor, and handling of the element may be difficult.

The sintered body as described above can be obtained by the following process. First, a powder of a metal oxide selected from those as enumerated above or a mixture of more than one such powder is prepared as a starting material. If a mixture of more than one powder is to be used, the powder of each metal oxide is measured, and the respective powders are mixed well in a ball mill together with ethyl alcohol or ethylene glycol. The resultant mixture is dried. If a particularly stable sintered body is desired, the mixture is dried and is thereafter presintered at 700° to 1,000° C. The presintered body is pulverized to provide a raw material powder. The resultant powder is then kneaded with a binder such as polyvinyl alcohol, polyethylene glycol or liquid paraffin. The kneaded substance is dried with air, and molded in a predetermined mold at room temperature into a plate or block shape. The molded body is then sintered by a known method to provide a sintered element. The resultant sintered element must have a suitable porous structure. According to the present invention, the sintered element preferably has a porous structure having a pore diameter of 100 nm or more and a porosity of 10 to 45%.

A sintered element having a porous structure according to the present invention is generally obtained by setting, in the manufacturing process as described above, a particle diameter of the raw material powder to be 0.1 to 2.0 $\mu$m, the molding pressure of the kneaded substance to be 500 to 2,000 kg/cm$^2$, the sintering temperature of the molded body to be 1,000° to 1,300° C., and the sintering time to be 0.5 to 2 hours.

A pair of electrodes are formed on one or both surfaces of the sintered element thus obtained by applying a conventional paste, such as a gold paste, a platinum paste, a ruthenium paste, or a carbon paste, at predetermined portions of the sintered body, and baking the applied paste. A simple substance or an oxide of at least one of phosphorus and sulfur, and copper ions are carried on the surface of and on the pore inner surfaces of the sintered body to provide a humidity-sensitive element of the present invention.

According to the present invention, carrying of a simple substance or an oxide of phosphorus or sulfur and of carrying of copper ions on a sintered element can be performed in the following manner. A sintered element obtained in the manner as described above is impregnated with a liquid containing copper ions and at least one of phosphorus and sulfur, and the liquid is then heated and thermally decomposed at a predetermined temperature.

In this case, the impregnating liquid is a liquid which upon a heat treatment leaves a simple substance or an oxide of phosphorus and/or sulfur and a copper ion compound on the surface or pore inner surfaces of the sintered element. If a substrate containing phosphorus or sulfur and copper ions is a liquid, it can be directly used. However, if such a substance is a solid substance, it can be dissolved in water or a suitable organic solvent to provide a solution.

Examples of a liquid containing phosphorus may include triethyl phosphite, trimethyl phosphite, tributyl phosphite, tri-p-cresyl phosphite, tri-o-cresyl phosphite, an aqueous solution of orthophosphoric acid, an aqueous solution of phosphorous acid, and an aqueous solution of pyrophosphoric acid.

Examples of a liquid containing sulfur may include ethyl sulfide, vinyl sulfide, phenyl sulfide, a solution of benzyl sulfide, methyl sulfide, a solution of triethyl phosphine sulfide, and diethyl sulfide.

Examples of a liquid containing copper ions may include aqueous solutions of a copper compound such as copper carbonate, copper chloride, copper citrate, copper cyanide, copper formate, copper hydroxide, copper carbonate hydroxide, copper nitrate, copper oxalate, copper phosphate, copper sulfide, or copper sulfate.

When a sintered element is impregnated with such a liquid, it is preferably impregnated with a mixture of such liquids mixed in a predetermined ratio. In this case, the mixture of the liquids may preferably be left to stand over 24 hours after being mixed, before it is used for impregnation. In order to perform uniform impregnation of the sintered element to a central portion thereof, impregnation is preferably performed under a reduced pressure or in a vacuum.

The sintered element is subjected to a heat treatment at a predetermined temperature to provide a sintered body. Upon this heat treatment, the impregnating liquid in the sintered element thermally decomposes to attach a simple substance or an oxide of at least one of phosphorus and sulfur and a copper ion compound on the surface and pore inner surfaces of the sintered element. According to the present invention, the heating temperature is set to be higher than the thermal decomposition temperatures of the components of the liquid. However, the heating temperature has a higher limit of about 700° C. and is preferably about 550° C.

A simple substance or oxide of at least one or phosphorus and sulfur used in a humidity-sensitive element of the present invention is preferably carried in the amount (the amount of phosphorus or sulfur) of 0.1 to 2.0% by weight based on the weight of the sintered element. When the carried amount is less than 0.1% by weight, the amount of such an element or oxide attached to the surface and pore inner surfaces of the sintered element is too small and stable humidity-sensitive characteristics may not be obtained. However, when the amount of such an element or oxide exceeds 2.0% by weight, the resistance of the overall element is significantly increased to render humidity measurement difficult.

The copper ions are preferably carried on the sintered element in the amount of 0.1 to 4.0% by weight. When the amount of copper ions carried is less than 0.1% by weight, it is too small and a drift under high humidities may not be improved. When the amount of copper ions exceeds 4.0% by weight, the number of digits defining a range of resistance change within a humidity range of 30%RH and 50%RH is small.

In the humidity-sensitive element of the present invention having the structure as described above, the humidity-sensitive characteristics are improved and a drift at a high humidity is small.

EXAMPLE 1

(i) Preparation of Zinc Oxide Sintered Element

After drying a powder of zinc oxide having a particle diameter of 0.1 to 2.0 μm at 150° C. for 2 hours, it is milled together with 8% by weight of 5% polyvinyl alcohol solution by a mill for about 20 minutes. The resultant kneaded substance was filled in a cylindrical mold and was molded at a pressure of 1,000 kg/cm$^2$ at a room temperature (25° C.) to provide a disc. The molded disc was then heat-treated at 1,100° C. for 1 hour in an electric furnace (air atmosphere) to provide a disc-shaped sintered element. The sintered element was polished by a SiC abrasive of #3,000 to provide a sintered disc having a diameter of 10 mm and a thickness of 0.5 mm. The sintered disc was measured by a mercury porosimeter to have a porosity of 25%.

A gold paste was applied on each surface of the sintered disc and was baked at 750° C. to form gold electrodes of 8.0 mm diameter.

(ii) Carrying of Phosphorus & Copper Ions on Sintered Disc

Triethyl phosphite containing 18% by weight of phosphorus and a copper chloride aqueous solution of 0.2 molarity were mixed well in equal amounts. The resultant solution was left to stand for 2 days and was then used for impregnation of the disc obtained above. The disc was immersed in the solution at $10^{-3}$ Torr for 60 minutes. The impregnated disc was drained and was dried at 100° C. for 30 minutes. The disc was then heat-treated at 550° C. for 20 minutes in an electric furnace (air atmosphere) to provide a humidity-sensitive element. Elementary analysis of the humidity-sensitive element by the conventional procedures revealed that 0.8% by weight of phosphorus and 2.0% by weight of copper were carried on the element.

Platinum wires as lead wires were connected to the gold electrodes on the two surfaces of the element of Example 1 and were also connected to an impedance measurement circuit. The humidity-sensitive element was placed in a thermostat kept at a constant humidity. The relationship (initial humidity-sensitive characteristics) between relative humidity (%) at 25° C. and electric resistance (kΩ) measured by the impedance measurement circuit are obtained as seen by curve (A) in FIG. 1.

Figure 1:
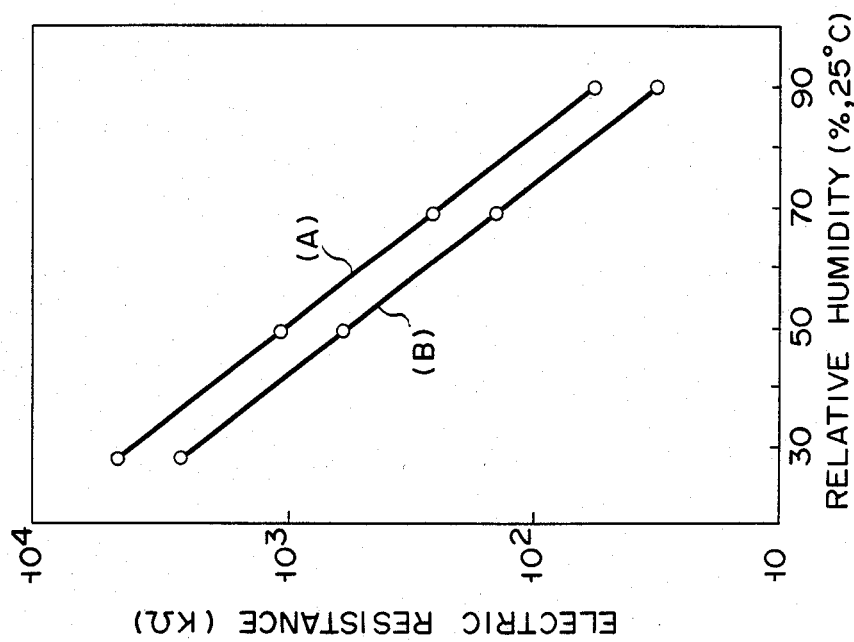
FIG. 1 is a graph showing the initial humidity-sensitive characteristics of a humidity-sensitive element in Example 1 of the present invention, and the same characteristics after the element is left to stand at 40° C. at 90%RH for 200 hours.

After the same element was left to stand at 40° C. at 90%RH for 200 hours, the same characteristics at 25° C. were measured and the characteristics as indicated by curve (B) in FIG. 1 were obtained. For the purpose of comparison, the initial humidity-sensitive characteristics of an element obtained by impregnating a sintered element with only phosphorus and the characteristics of the same element after being left to stand at 40° C. at 90%RH for 200 hours were measured. The results as indicated by curves (C) and (D) in FIG. 2 were obtained (Comparative Example 1). A comparison of the initial characteristics and the characteristics after being left at a high humidity reveals that a maximum value (drift) of the difference in the relative humidity corresponding to a certain electric resistance after the element is left at a high humidity is 8% in the element of Example 1, while it is 15% in the element of Comparative Example 1. It is seen from this that the element of the present invention has a higher performance than that of the conventional element.

When the element of Example 1 was placed in the ambient air, the characteristics substantially returned to the initial characteristics.

EXAMPLE 2

A sintered disc of zinc oxide was prepared following the same procedures as in Example 1. A sulfur-carrying humidity-sensitive element was subsequently prepared following the same procedures as in Example 1 except that the impregnating liquid consisted of a mixture of ethyl sulfide containing 35% by weight of sulfur and a copper nitrate solution having a 0.2 molarity. The resultant element was found to have a carried amount of sulfur of 1.9% by weight and a carried amount of copper of 2.1% by weight.

As in Example 1, the element was left to stand at 40° C. for 90%RH, and humidity-sensitive characteristics were measured. The electrical resistances of 2,000 k$\Omega$ and 20 k$\Omega$ of the element measured at 25° C. at relative humidities of 30% and 90%, respectively, were changed to 1,200 k$\Omega$ and 18 k$\Omega$ after the element was being left to stand at a high humidity of 90%RH. The drift was as small as +7%.

EXAMPLE 3

Sintered discs of zinc oxide were prepared following the same procedures as in Example 1. Triethyl phosphite was mixed with copper chloride of varying concentrations to provide impregnating liquids. Each sintered disc was impregnated with a corresponding impregnating liquid and was then heat-treated at a temperature of 550° C. The initial characteristics of the respective humidity-sensitive elements obtained at humidities of 30%, 50%, 70%, and 90% were determined from the relationship between the resistances and the amounts of copper carried on the sensors. The results shown in FIG. 3 were obtained. Curve $D_{30}$ in FIG. 3 shows the resistance when the humidity was 30%, curve $D_{50}$ shows the same when the humidity was 50%, curve $D_{70}$ shows the same when the humidity was 70%, and curve $D_{90}$ shows the same when the humidity was 90%. When the amount of copper carried is 4% by weight or more, substantially no change in the electric resistance is observed within the relative humidity range of 30%RH to 50%RH, thus rendering humidity detection practically impossible. When the amount of copper carried is 0.1% or less, a drift as large as +15% is obtained after the element is left to stand at 40° C. at 90%RH and so the effect of the present invention was scarcely obtained.

EXAMPLES 4 TO 17

Various sintered bodies were prepared following the same procedures as in Example 1 except that the starting materials were respectively powders (0.1 to 2.0 $\mu$m particle size) of ferric oxide, stannic oxide, chromium oxide, tri-iron tetroxide, an equimolar mixture of magnesia and chromium oxide, an equimolar mixture of barium oxide and titanium dioxide, and an equimolar mixture of manganese oxide and ferric oxide. Phosphorus or sulfur and copper were carried on the respective sintered bodies and the amounts of these substances carried (% by weight) were measured.

The resultant elements of Examples 4 to 17 were left to stand at a high humidity under the same conditions as in Example 1, and drifts were examined. The obtained results are shown in Table 1 below.

TABLE 1

| | Composition of humidity-sensitive element | Phosphorus and sulfur | | Copper Carried amount (wt %) | Drift (%) after 40° C., 90% RH × 200 hrs |
|---|---|---|---|---|---|
| | | Type | Carried amount (wt %) | | |
| Example 4 | $Fe_2O_3$ | Phosphorus | 0.7 | 2.2 | +6 |
| Example 5 | $SnO_2$ | Phosphorus | 0.7 | 1.5 | +8 |
| Example 6 | $Cr_2O_3$ | Phosphorus | 0.7 | 3.2 | +9 |
| Example 7 | $Fe_3O_4$ | Phosphorus | 0.6 | 0.5 | +10 |
| Example 8 | $MgO.Cr_2O_3$ | Phosphorus | 0.8 | 2.6 | +7 |
| Example 9 | $BaO.TiO_2$ | Phosphorus | 0.8 | 1.2 | +8 |
| Example 10 | $MnO.Fe_2O_3$ | Phosphorus | 0.8 | 3.7 | +8 |
| Example 11 | $Fe_2O_3$ | Sulfur | 0.7 | 2.2 | +7 |
| Example 12 | $SnO_3$ | Sulfur | 0.7 | 1.5 | +7 |
| Example 13 | $Cr_2O_3$ | Sulfur | 0.7 | 2.0 | +8 |
| Example 14 | $Fe_3O_4$ | Sulfur | 0.6 | 3.2 | +8 |
| Example 15 | $MgO.Cr_2O_3$ | Sulfur | 0.8 | 0.5 | +7 |
| Example 16 | $BaO.TiO_2$ | Sulfur | 0.8 | 2.6 | +6 |
| Example 17 | $MnO.Fe_2O_3$ | Sulfur | 0.8 | 1.2 | +7 |

EXAMPLES 18 TO 24

Various sintered discs were prepared following the same procedures as in Example 1 except that the starting materials were powders (0.1 to 2.0 $\mu$m particle size) of zinc oxide, ferric oxide, stannic oxide, chromium oxide, tri-iron tetroxide, an equimolar mixture of magnesium oxide and chromium oxide, and an equimolar mixture of manganese oxide and ferric oxide. The resultant discs were immersed in an equimolar solution (mixing ratio based on volume of triethyl phosphite and ethyl sulfide of 1:1), of the triethyl phosphite containing 18% by weight of phosphorus and the ethyl sulfide containing varying amounts of sulfur. The atmosphere was maintained at $10^{-3}$ Torr for 20 minutes to complete impregnation.

The discs were drained and were dried at 100° C. for 1 hour. The dried discs were then placed in an electric furnace (air atmosphere) and were heat-treated at 550°

C. for 30 minutes to provide humidity-sensitive elements of Examples 18 to 24.

The resultant humidity-sensitive elements of Examples 18 to 24 were measured for their initial humidity-sensitive characteristics and for their characteristics after being left to stand at 40° C. at 90%RH for 200 hours in the same manner as in Example 1. The characteristics obtained after such humidity test were compared with the initial characteristics, and drifts under high humidity were determined. The drifts fell within the range of +10% to +6%.

TABLE 2

|  | Composition of humidity-sensitive element | Phosphorus and sulfur Total carried amount (wt %) | Copper Carried amount (wt %) | Drift (%) after 40° C., 90% RH × 1 week |
|---|---|---|---|---|
| Example 18 | ZnO | 0.8 | 2.2 | +6 |
| Example 19 | $Fe_2O_3$ | 0.7 | 2.3 | +6 |
| Example 20 | $SnO_2$ | 0.7 | 1.0 | +7 |
| Example 21 | $Cr_2O_3$ | 0.7 | 3.0 | +8 |
| Example 22 | $Fe_3O_4$ | 0.7 | 0.6 | +9 |
| Example 23 | $MgO.Cr_2O_3$ | 0.8 | 2.3 | +7 |
| Example 24 | $MnO.Fe_2O_3$ | 0.8 | 3.4 | +10 |

EXAMPLE 25

(i) Preparation of Sintered Element (10 mol % of zinc oxide, 80 mol % of titanium dioxide, and 10 mol % of chromium oxide)

Fine powders of the respective oxides were measured in the above molar ratios and were then mixed with ethyl alcohol in a Teflon pot for 24 hours. After the resultant mixture was dried, polyvinyl alcohol was added. The resultant mixture was pelletized by a mill, placed in a cylindrical mold and molded at a pressure of 1,000 kg/cm². The molded body was sintered at 1,100° C. for 2 hours in an electric furnace. The obtained sintered body was polished to provide a disc having a diameter of 10 mm and a thickness of 0.5 mm. A ruthenium oxide paste was applied on each surface of the sintered disc and was baked at 700° C. to form electrodes of 8.0 mm diameter.

(ii) Carrying of Phosphorus and Copper on Sintered Disc

Triethyl phosphite containing 18% by weight of phosphorus and 0.2 molarity copper nitrate solution were mixed well in equal volume to provide a mixed solution. The sintered disc obtained above was immersed in the solution and the pressure was kept at $10^{-3}$ Torr for 20 minutes to complete impregnation. The sintered disc was drained and was dried at 100° C. The disc was then heat-treated at 550° C. for 30 minutes in an electric furnace to provide a humidity-sensitive element. Elementary analysis of the element by a known method revealed that 0.8% by weight of phosphorus and 2.0% by weight of copper were carried on the disc.

Figure 4:
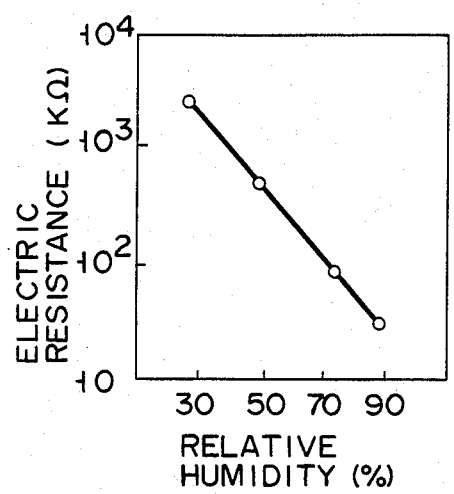
FIG. 4 is a graph showing the initial humidity-sensitive characteristics of a humidity-sensitive element of Example 25.
Figure 5:
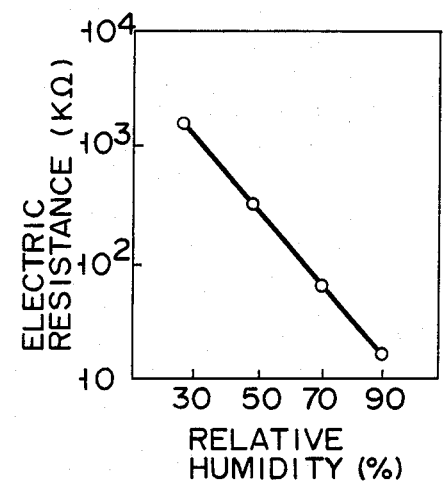
FIG. 5 is a graph showing the humidity-sensitive characteristics of the element of Example 25 after being left to stand at 40° C. at 90%RH for 1,000 hours.
Figure 6:
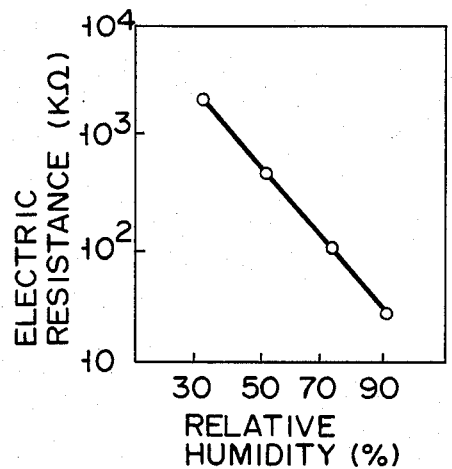
FIG. 6 is a graph showing the initial humidity-sensitive characteristics of a humidity-sensitive element of Comparative Example 2.
Figure 7:
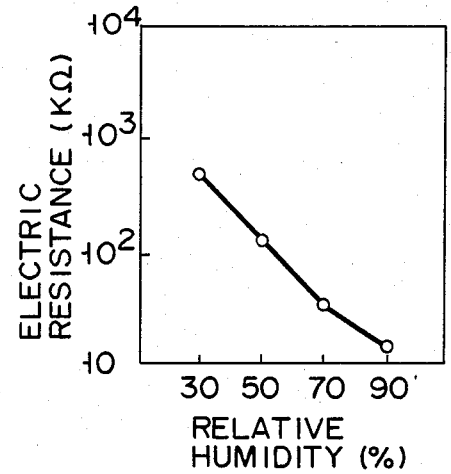
FIG. 7 is a graph showing the humidity-sensitive characteristics of the element of Comparative Example 2 after being left to stand at 40° C. at 90%RH for 1,000 hours.

When the initial humidity-sensitive characteristics of the resultant element were measured in the same manner as in Example 1, the results as shown in FIG. 4 were obtained. After the element was left to stand at 40° C. at 90%RH for 1,000 hours, it was then measured for its resistance at various humidities at 25° C. Then, the results as shown in FIG. 5 were obtained. For the purpose of comparison, a humidity-sensitive element carrying only phosphorus obtained by impregnating a sintered body consisting of 10 mol % of zinc oxide, 80 mol % of titanium dioxide and 10 mol % of chromium oxide with only a triethyl phosphite solution (Comparative Example 2) was measured for its initial characteristics and its characteristics at various humidities at 25° C. after being left to stand at 40° C. at 90%RH for 1,000 hours. The obtained results are shown in FIGS. 6 and 7.

As seen from FIGS. 4 to 7, a humidity-sensitive element of the present invention exhibit stable humidity-sensitive characteristics at 40° C. at 90%RH and therefore has an extremely high reliability.

EXAMPLES 26 TO 31

Humidity-sensitive elements having the compositions as shown in Table 3 below were prepared in accordance with the same procedures as in Example 25.

The three types of elements obtained were measured for their initial characteristics at 25° C. as in Example 1 and for their characteristics after being left to stand at 40° C. at 90%RH for 1,000 hours. Table 3 below shows the initial resistance at 30%RH, the initial resistance at 90%RH, and resistances at these humidities after the elements were placed at 90%RH humidity for 1,000 hours. Table 3 also shows the drift.

TABLE 3

| | Specifications/characteristics | | | | | | |
|---|---|---|---|---|---|---|---|
| | Composition of sintered body (mol %) | | | Type of impregnating solution | | Carried amount of phosphorus and | Carried amount |
| No. | ZnO | $TiO_2$ | $Cr_2O_3$ | I | II | sulfur (wt %) | of copper (wt %) |
| Example 26 | 5 | 90 | 5 | Triethyl phosphite | Copper nitrate | 0.8 | 2.0 |
| Example 27 | 50 | 30 | 20 | Triethyl phosphite | Copper nitrate | 0.8 | 2.0 |
| Example 28 | 10 | 80 | 10 | Ethyl sulfide | Copper nitrate | 0.8 | 2.0 |
| Example 29 | 2 | 96 | 2 | Triethyl phosphite | Copper nitrate | 0.8 | 2.0 |
| Example 30 | 60 | 20 | 20 | Triethyl phosphite | Copper nitrate | 0.8 | 2.0 |
| Example 31 | 10 | 80 | 10 | Triethyl phosphite | Copper nitrate | 0.8 | 5.0 |

| Specifications/characteristics | |
|---|---|
| Initial Sensitivity | Sensitivity after 40° C., 90% RH × 1,000 hrs |

TABLE 3-continued

| No. | Resistance (kΩ) at 25° C., 30% RH | Resistance (kΩ) at 25° C., 90% RH | Resistance (kΩ) at 25° C., 30% RH | Resistance (kΩ) at 25° C., 90% RH | Drift (%) after 40° C., 90% RH × 1,000 hrs |
|---|---|---|---|---|---|
| Example 26 | 1,700 | 60 | 1,100 | 40 | 7 |
| Example 27 | 2,400 | 75 | 1,900 | 55 | +9 |
| Example 28 | 2,300 | 95 | 1,700 | 72 | +9 |
| Example 29 | 5,300 | 140 | 2,400 | 90 | +14 |
| Example 30 | 3,200 | 180 | 2,700 | 90 | +18 |
| Example 31 | 1,800 | 140 | 1,000 | 80 | +16 |

It is seen from Table 3 above that when a metal oxide sintered body consists of 5 to 50 mol % of ZnO, 30 to 90 mol % of $TiO_2$ and 5 to 20 mol % of $Cr_2O_3$ as in Examples 26 to 28, the resultant element has a sufficiently wide range of resistance change and has an improved drift after being left to stand under a high humidity.

EXAMPLES 32 TO 36

Humidity-sensitive elements having the compositions shown in Table 4 below were prepared following the same procedures as in Example 25. The three types of humidity-sensitive elements obtained were measured for their initial characteristics and for their characteristics after being left to stand at 40° C. at 90%RH for 1,000 hours as in Example 1. The obtained results are also shown in Table 4.

TABLE 4

| | Specifications/characteristics | | | | | |
|---|---|---|---|---|---|---|
| | Composition of sintered body (mol %) | | Type of impregnating solution | | Carried amount of | Carried amount |
| No. | $TiO_2$ | $Al_2O_3$ | I | II | phosphorus (wt %) | of copper (wt %) |
| Example 32 | 99 | 1 | Triethyl phosphite | Copper nitrate | 0.8 | 2.0 |
| Example 33 | 70 | 30 | Triethyl phosphite | Copper nitrate | 0.8 | 2.0 |
| Example 34 | 90 | 10 | Triethyl phosphite | Copper nitrate | 0.8 | 2.0 |
| Example 35 | 99.5 | 0.5 | Triethyl phosphite | Copper nitrate | 0.8 | 2.0 |
| Example 36 | 60 | 40 | Triethyl phosphite | Copper nitrate | 0.6 | 2.0 |

| | Specifications/characteristics | | | | |
|---|---|---|---|---|---|
| | Initial sensitivity | | Sensitivity after 40° C., 90% RH × 1,000 hrs | | |
| No. | Resistance (kΩ) at 30% RH | Resistance (kΩ) at 90% RH | Resistance (kΩ) at 30% RH | Resistance (kΩ) at 90% RH | Drift % after 40° C., 90% RH × 1,000 hrs |
| Example 32 | 2,900 | 32 | 2,000 | 23 | +7 |
| Example 33 | 1,700 | 8.5 | 1,050 | 51 | +8 |
| Example 34 | 2,600 | 65 | 1,400 | 49 | +9 |
| Example 35 | 5,300 | 160 | 3,400 | 82 | +14 |
| Example 36 | 3,600 | 85 | 2,400 | 49 | +11 |

EXAMPLE 37

Humidity-sensitive elements having the compositions shown in Table 5 below were prepared following the same procedures as in Example 25. The three types of humidity-sensitive elements were measured for their initial characteristics and their characteristics after being left to stand at 40° C. at 90%RH for 1,000 hours as in Example 1. The obtained results and the drifts are also shown in Table 5.

TABLE 5

| | Specifications/characteristics | | | | | |
|---|---|---|---|---|---|---|
| | Composition of sintered body (mol %) | | Type of impregnating solution | | Carried amount of | Carried amount |
| No. | $TiO_2$ | MgO | I | II | phosphorus (wt %) | of copper (wt %) |
| Example 37 | 99 | 1 | Triethyl phosphite | Copper nitrate | 0.8 | 2.0 |
| Example 38 | 70 | 30 | Triethyl phosphite | Copper nitrate | 0.8 | 2.0 |
| Example 39 | 90 | 10 | Triethyl phosphite | Copper nitrate | 0.8 | 2.0 |
| Example 40 | 99.5 | 0.5 | Triethyl phosphite | Copper nitrate | 0.8 | 2.0 |
| Example 41 | 60 | 40 | Triethyl phosphite | Copper nitrate | 0.8 | 2.0 |

| | Specifications/characteristics | |
|---|---|---|
| | Initial sensitivity | Sensitivity after 40° C., 90% RH × 1,000 hrs |

TABLE 5-continued

| No. | Resistance (kΩ) at 30% RH | Resistance (kΩ) at 90% RH | Resistance (kΩ) at 30% RH | Resistance (kΩ) at 90% RH | Drift (%) after 40° C., 90% RH × 1,000 hrs |
|---|---|---|---|---|---|
| Example 37 | 3,000 | 41 | 2,300 | 31 | +6 |
| Example 38 | 4,700 | 24 | 1,400 | 19 | +7 |
| Example 39 | 2,300 | 37 | 1,800 | 29 | +6 |
| Example 40 | 5,500 | 160 | 2,900 | 82 | +13 |
| Example 41 | 4,100 | 52 | 2,400 | 28 | +14 |

It is seen from Tables 4 and 5 above that when a porous metal oxide sintered body consists of 99 to 70 mol % of titanium dioxide and 1 to 30 mol % of alumina or magnesia as in Examples 29 to 34 described above, the resultant element has a sufficiently wide range of resistance change and an improved drift after being left to stand at a high humidity for a long period of time.

EXAMPLE 42

(i) Preparation of Sintered Element (90 mol % of titanium (IV) dioxide and 10 mol % of chromium (III) oxide)

Fine powders of the respective oxides were measured in the above molar ratios and were then mixed with ethyl alcohol in a Teflon pot for 24 hours. After the resultant mixture was dried, polyvinyl alcohol was added. The mixture was pelletized by a mill, placed in a cylindrical mold and molded at a pressure of 1,000 kg/cm². The molded body was sintered at 1,100° C. for 2 hours in an electric furnace. The obtained sintered body was polished to provide a disc having a diameter of 10 mm and a thickness of 0.5 mm. A ruthenium oxide paste was applied on each surface of the sintered disc and was baked at 700° C. to form electrodes of 8.0 mm diameter.

(ii) Carrying of Phosphorus and Copper on Sintered Disc

Triethyl phosphite containing 18% by weight of phosphorus and 0.2 molarity copper nitrate solution were mixed well in equal volume to provide a mixed solution. The sintered disc obtained above was immersed in the solution and the pressure was kept at $10^{-3}$ Torr for 20 minutes to complete impregnation. The sintered disc was drained and was dried at 100° C. The disc was then heat-treated at 550° C. for 30 minutes in an electric furnace to provide a humidity-sensitive element. Elementary analysis of the element by a known method revealed that 0.8% by weight of phosphorus and 2.0% by weight of copper were carried on the disc.

Figure 8:
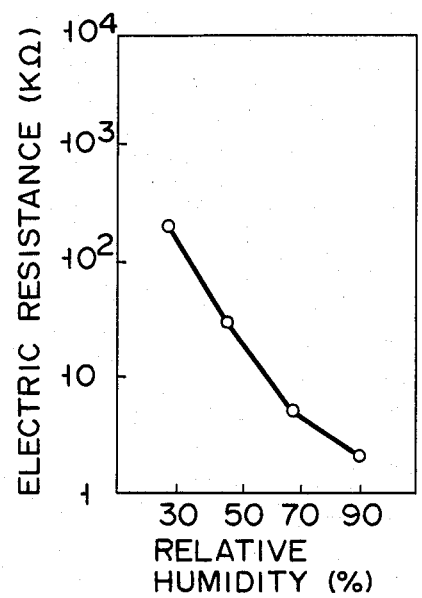
FIG. 8 is a graph showing the initial humidity-sensitive characteristics of a humidity-sensitive element of Example 42.
Figure 9:
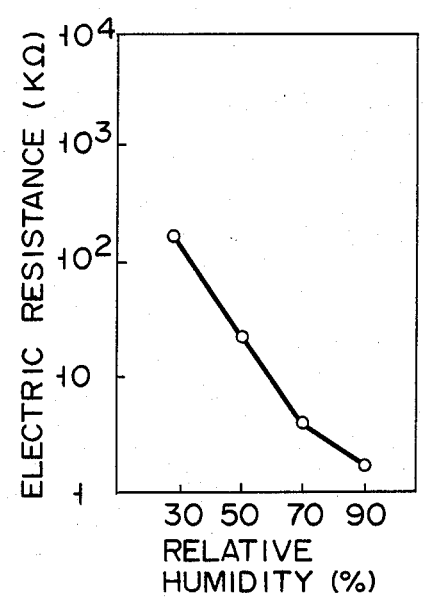
FIG. 9 is a graph showing the humidity-sensitive characteristics of the element of Example 42 after being left to stand at 40° C. at 90%RH for 1,000 hours.
Figure 10:
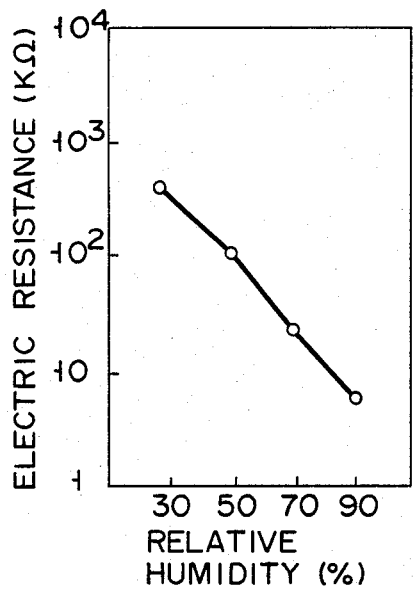
FIG. 10 is a graph showing the initial humidity-sensitive characteristics of a humidity-sensitive element of Comparative Example 3.
Figure 11:
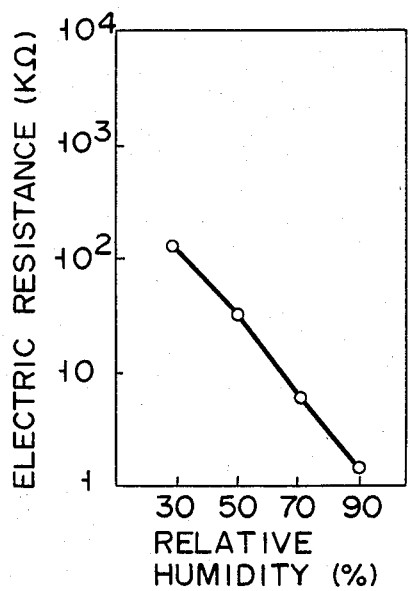
FIG. 11 is a graph showing the humidity-sensitive characteristics of the element of Comparative Example 3 after being left to stand at 40° C. at 90%RH for 1,000 hours.

When the initial humidity-sensitive characteristics of the resultant element were measured in the same manner as in Example 1, the results as shown in FIG. 8 were obtained. After the element was left to stand at 40° C. at 90%RH for 1,000 hours, it was then measured for its resistance at various humidities at 25° C. Then, the results as shown in FIG. 9 were obtained. For the purpose of comparison, an element carrying only phosphorus and obtained by impregnating a sintered body consisting of 90 mol % of titanium (IV) dioxide and 10 mol % of chromium (III) oxide with only a triethyl phosphite solution (Comparative Example 3) was measured for its initial characteristics and its characteristics at 25° C. after being left to stand at 40° C. at 90%RH for 1,000 hours. The obtained results are shown in FIGS. 10 and 11.

As seen from FIGS. 8 to 11, a humidity-sensitive element of the present invention exhibit stable humidity-sensitive characteristics at 40° C. at 90%RH and therefore has an extremely high reliability.

EXAMPLES 43 TO 56

Humidity-sensitive elements having the compositions as shown in Table 6 below were prepared in accordance with the same procedures as in Example 42.

The nine types of elements obtained were measured for their initial characteristics at 25° C. as in Example 1 and for their characteristics (resistances) at 25° C. and 30%RH and at 25° C. and 90%RH after being left to stand at 40° C. at 90%RH for 1,000 hours. Table 6 below shows the initial resistance at 30%RH, the initial resistance at 90%RH, and the resistances after the elements were placed at 90%RH humidity.

TABLE 6

| | Specifications/characteristics | | | | |
|---|---|---|---|---|---|
| | Composition of sintered body | | Type of impregnating solution | | Carried amount of phosphorus and | Carried amount |
| No. | (mol %) | | I | II | sulfur (wt %) | of copper (wt %) |
| Example 43 | 99 (TiO$_2$) | 1 (Cr$_2$O$_3$) | Triethyl phosphite | Copper nitrate | 0.8 | 2.0 |
| Example 44 | 70 (TiO$_2$) | 30 (Cr$_2$O$_3$) | Triethyl phosphite | Copper nitrate | 0.8 | 2.0 |
| Example 45 | 90 (TiO$_2$) | 10 (Cr$_2$O$_3$) | Ethyl sulfide | Copper nitrate | 0.8 | 2.0 |
| Example 46 | 90 (TiO$_2$) | 10 (MoO$_3$) | Ethyl sulfide | Copper nitrate | 0.8 | 2.0 |
| Example 47 | 70 (TiO$_2$) | 30 (MoO$_3$) | Triethyl phosphite | Copper nitrate | 0.8 | 2.0 |
| Example 48 | 70 (TiO$_2$) | 30 (WO$_3$) | Triethyl phosphite | Copper nitrate | 0.8 | 2.0 |
| Example 49 | 70 (TiO$_2$) | 30 (Ta$_2$O$_5$) | Triethyl phosphite | Copper nitrate | 0.8 | 2.0 |
| Example 50 | 70 (TiO$_2$) | 30 (Nb$_2$O$_5$) | Triethyl phosphite | Copper nitrate | 0.8 | 2.0 |
| Example 51 | 70 (TiO$_2$) | 30 (V$_2$O$_5$) | Triethyl phosphite | Copper nitrate | 0.8 | 2.0 |
| Example 52 | 99.5 | 0.5 | Triethyl | Copper | 0.8 | 2.0 |

TABLE 6-continued

| No. | (TiO$_2$) | (Cr$_2$O$_3$) | phosphite | nitrate | | |
|---|---|---|---|---|---|---|
| Example 53 | 60 | 40 | Triethyl phosphite | Copper nitrate | 0.8 | 2.0 |
| | (TiO$_2$) | (Cr$_2$O$_3$) | | | | |
| Example 54 | 90 | 10 | Triethyl phosphite | Copper nitrate | 0.8 | 5.0 |
| | (TiO$_2$) | (Cr$_2$O$_3$) | | | | |
| Example 55 | 99.5 | 0.5 | Triethyl phosphite | Copper nitrate | 0.8 | 2.0 |
| | (TiO$_2$) | (MoO$_3$) | | | | |
| Example 56 | 60 | 40 | Triethyl phosphite | Copper nitrate | 0.8 | 2.0 |
| | (TiO$_2$) | (MoO$_3$) | | | | |

| | Specifications/characteristics | | | | |
|---|---|---|---|---|---|
| | Initial sensitivity | | Sensitivity after 40° C., 90% RH × 1,000 hrs | | |
| No. | Resistance (kΩ) at 25° C., 30% RH | Resistance (kΩ) at 25° C., 90% RH | Resistance (kΩ) at 25° C., 30% RH | Resistance (kΩ) at 25° C., 90% RH | Drift (%) after 40° C., 90% RH × 1,000 hrs |
| Example 43 | 1,800 | 67 | 1,200 | 46 | +7 |
| Example 44 | 330 | 3.5 | 290 | 2.5 | +6 |
| Example 45 | 470 | 5.1 | 380 | 3.2 | +7 |
| Example 46 | 570 | 15 | 400 | 10 | +6 |
| Example 47 | 750 | 30 | 520 | 22 | +7 |
| Example 48 | 920 | 20 | 600 | 12 | +8 |
| Example 49 | 810 | 15 | 600 | 9.9 | +7 |
| Example 50 | 700 | 24 | 500 | 16 | +6 |
| Example 51 | 990 | 41 | 690 | 30 | +7 |
| Example 52 | 3,800 | 165 | 1,800 | 73 | +17 |
| Example 53 | 2,900 | 120 | 1,500 | 89 | +18 |
| Example 54 | 740 | 91 | 530 | 47 | +14 |
| Example 55 | 4,200 | 210 | 2,300 | 91 | +17 |
| Example 56 | 3,600 | 180 | 1,900 | 76 | +16 |

Humidity-sensitive elements having porous metallic oxide sintered bodies consisting of 99 to 70 mol % of TiO$_2$ and 1 to 30 mol % of an oxide or a mixture of more than one of Cr$_2$O$_3$, WO$_2$, MoO$_2$, Ta$_2$O$_5$, Nb$_2$O$_5$, and V$_2$O$_3$ have a sufficient resistance change range and an improved drift after being left to stand at a high humidity for a long period of time.

In the embodiment described above, the element was obtained by impregnating porous sintered bodies with various solutions. However, phosphorus or sulfur and copper can be carried on a metal oxide layer formed on a substrate of alumina or magnesia by a thick film forming method or a thin film forming method such as printing/baking, sputtering or the like.

What is claimed is:

1. A humidity-sensitive element comprising:
   a porous metal oxide sintered body;
   a material selected from the group consisting of phosphorus, sulfur and oxides thereof, said simple material carried on said porous metal oxide sintered body; and
   copper ions carried on said porous metal oxide sintered body.

2. The humidity-sensitive element according to claim 1, wherein said porous metal oxide sintered body consists of 5 to 50 mol % of zinc oxide, 30 to 90 mol % of titanium dioxide, and 5 to 20 mol % of chromium oxide.

3. The humidity-sensitive element according to claim 1, wherein said porous metal oxide sintered body consists of 70 to 99 mol % of titanium dioxide and 1 to 30 mol % of alumina.

4. The humidity-sensitive element according to claim 1, wherein said porous metal oxide sintered body consists of 70 to 99 mol % of titanium dioxide and 1 to 30 mol % of magnesium oxide.

5. The humidity-sensitive element according to claim 1, wherein said porous metal oxide sintered body consists of 70 to 99 mol % of titanium dioxide and 1 to 30 mol % of at least one oxide selected from the group consisting of chromium oxide, tungsten oxide, molybdenum oxide, tantalum oxide, niobium oxide, and vanadium oxide.

6. The humidity-sensitive element according to claim 1, wherein said material selected from the group consisting of phosphorus, sulfur and oxides thereof, is carried on said porous metal oxide sintered body in an amount of 0.1 to 2.0% by weight calculated in terms of an amount of phosphorus or sulfur based on a weight of said porous metal oxide sintered body, and said copper ions are carried on said porous metal oxide sintered body in an amount of 0.1 to 4.0% by weight calculated in terms of an amount of copper based on the weight of said porous metal oxide sintered body.

7. The humidity-sensitive element according to claim 1, wherein said porous metal oxide sintered body has a pore diameter of not less than 100 nm and a porosity of 10 to 45%.

* * * * *